United States Patent [19]

Burkhardt et al.

[11] Patent Number: 4,597,849

[45] Date of Patent: Jul. 1, 1986

[54] GAS SENSOR SUITABLE FOR ENGINE EXHAUST GASES

[75] Inventors: Joachim Burkhardt, Fellbach; Manfred Dreyer, Kornwestheim; Dittmar Klett, Pleidelsheim; Helmut Weyl, Schwieberdingen, all of Fed. Rep. of Germany

[73] Assignee: Robert Bosch GmbH, Stuttgart, Fed. Rep. of Germany

[21] Appl. No.: 611,848

[22] Filed: May 18, 1984

[30] Foreign Application Priority Data

May 28, 1983 [DE] Fed. Rep. of Germany ....... 3319486

[51] Int. Cl.$^4$ ............................................ G01N 27/46
[52] U.S. Cl. .................................... 204/424; 204/427; 174/77 R
[58] Field of Search .......................... 204/15, 421–429; 174/74 R, 77 R

[56] References Cited

U.S. PATENT DOCUMENTS

| | | | |
|---|---|---|---|
| 3,152,057 | 10/1964 | Conger et al. | 204/435 |
| 3,530,849 | 9/1970 | Watanabe et al. | 204/435 |
| 3,959,107 | 5/1976 | Horner et al. | 204/435 |
| 4,116,798 | 9/1978 | Magar et al. | 204/435 |
| 4,123,131 | 10/1978 | Pearce et al. | 204/428 |
| 4,187,163 | 2/1980 | Steinke et al. | 204/428 |
| 4,328,296 | 5/1982 | Tanaka et al. | |
| 4,347,113 | 8/1982 | Fischer et al. | 204/428 |
| 4,362,609 | 12/1982 | Sano et al. | 204/428 |
| 4,370,213 | 1/1983 | Oki et al. | 204/428 |
| 4,399,320 | 7/1982 | Friese et al. | 204/428 |

Primary Examiner—T. Tung
Attorney, Agent, or Firm—Frishauf, Holtz, Goodman & Woodward

[57] ABSTRACT

The connection conductor leading from the connection end of a sensor element towards the end of the sensor remote from the gas to be measured is a metallic connection part (17) that is rigid against torsion and passes through the aperture (16) of the closure shell (14) where it is sealed by a bead-like element (41) having a tubular extension (48), beyond which the connection conductor has an axial internal connection surface for a cable (19). A sleeve (51) of yielding material (51) covers the adjoining ends of the cable and of the connecting conductor and an overlay shell (52) compresses the sleeve to make a tight seal, both around the cable and against the tubular end of the bead (41). The overlay shell snaps on to the tubular extension of the bead by interlocking annular sawtooth ridges.

13 Claims, 1 Drawing Figure

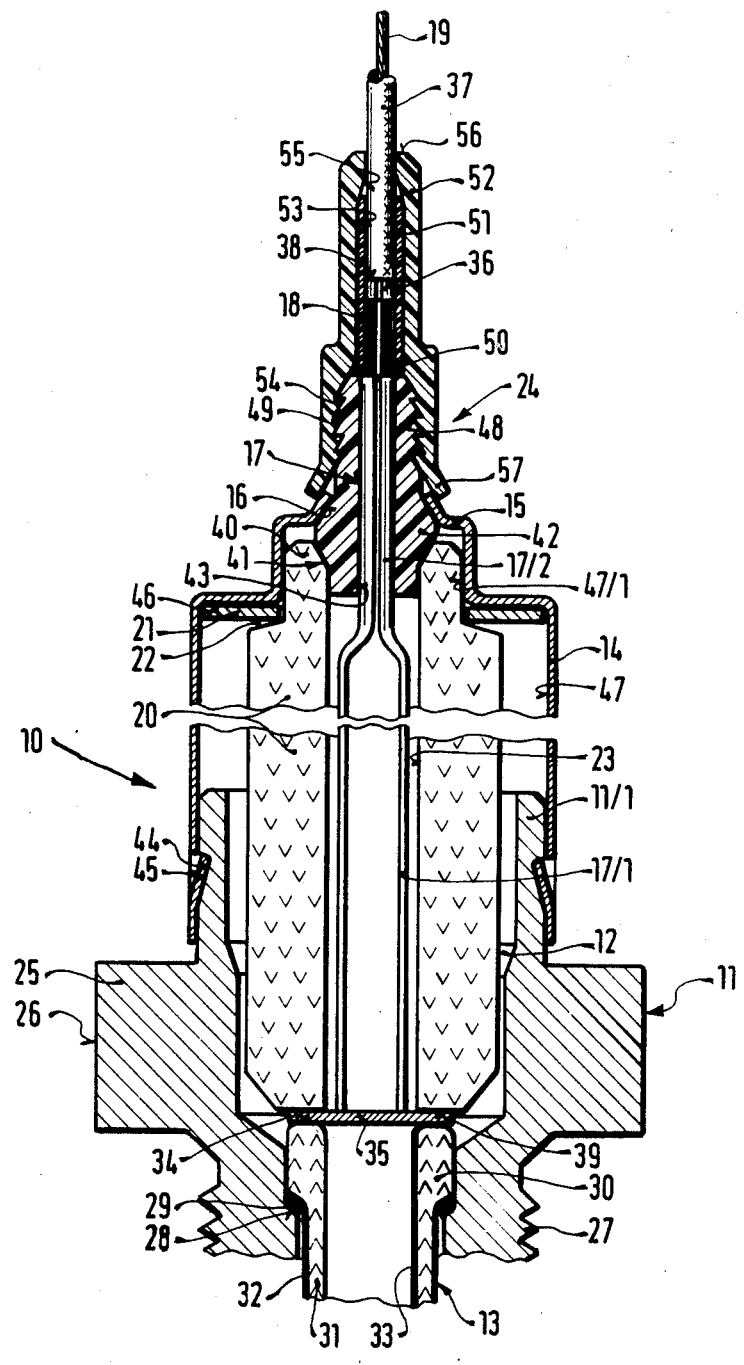

GAS SENSOR SUITABLE FOR ENGINE EXHAUST GASES

This invention concerns a gas sensor of the kind where the sensor element is held in a metallic casing which can be assembled into a duct carrying a gas to be measured and where at the end remote from the measurement gas there is a closure shell with an aperture at its tip, through which an electrical connection conductor runs with the seal element sealing both the conductor and the aperture in the closure shell.

U.S. Pat. No. 4,347,113 shows a gas sensor for exhaust gases of nternal combustion engines in which the connecting cable is fastened to a connecting part which at its measurement gas end is connected electrically to a sensor element, the connecting part being rigid against torsion, and the connecting cable leads out through a seal element in the bottom of a closure shell located away from the measurement gas. In this known configuration of the cable connection the degree of tightness of the seal is not satisfactory, and, furthermore, the connection between the connecting part and the connecting cable located in the interior of the sensor is troublesome to produce.

It is further known from U.S. Pat. No. 4,325,600 to insert a connection plug equipped with a cable and protective shell into a mating connector at the end section of a gas sensor which is remote from the measuring gas. Such a configuration is very expensive to produce, however.

SUMMARY OF THE INVENTION

It is an object of the present invention to provide a gas sensor of the general kind described above in which the feedthrough arrangement of the connecting conductor in the bottom of the closure shell away from the measurement gas is reliable and both simple and economical to produce.

Briefly, a metallic connecting part which is rigid against torsion and electrically connected to the sensor element is the connection conductor that leads centrally out of the metallic casing and of the interior of the closure shell. It has a sleeve-like connection area extending out of the endface of a seal element remote from the measurement gas. The connection cable is fixed in an electrically conducting manner axially within the seal element. A yielding sealing tube is disposed over the sleeve shaped connection region of the connecting part and over the measurement-gas-end section of the connecting cable which itself has an insulating covering. The yielding sealing tube is pressed together by means of an overlay shell in such a way that the midbore of the overlay shell surrounding the connection cable as well as the contact plane between the end surface of the sealing element and the end surface towards the measurement gas of the sealing tube are properly sealed.

It is furthermore advantageous for the sealing element to extend in the form of a hollow shaft and to be provided with coaxial external ring grooves or ridges of sawtooth profile and for the overlay shell to have similar coaxial internal features so that when it is slipped on into place these annular sawtoothed features of the overlay shell and of the hollow shaft of the seal element catch fast into each other.

BRIEF DESCRIPTION OF THE DRAWING

The invention is further described by way of illustrative example with reference to the annexed drawing, the single FIGURE of which shows a longitudinal section, on a magnified scale, with a mid-portion and an end portion, omitted, of a gas sensor according to the invention.

DESCRIPTION OF THE ILLUSTRATED EMBODIMENT

The gas sensor 10 shows in the drawing has a tubular metal casing 11, a sensor element 13 protruding out of the interior 12 of the metal casing 11 on the measuring gas side or end of the device. At its end away from the measurement gas it has a metallic enclosure shell or breech casing 14 having a hole 16 in its end wall 15 remote from the measurement gas. Electrically connected to the sensor element 13 is a connection part 17 that is rigid against twisting and is provided with a connection region 18 protruding out of the bottom hole 16 of the enclosing sleeve 14 for attachment of a conecting cable 19. In the interior 12 of the metal casing 11 is fixed a ceramic insulation tube 20, with a carrying shoulder 22 away from the measurement gas, which carries a ring-shaped spring element 21. The longitudinal bore 23 of the insulating tube 20 accepts the connection part 17 and the lower part of the seal assembly 24 of the gas sensor 10 at its extremity away from the measurement gas.

The metal casing 11 has an external flange 25 which is provided with a hexagonal exterior 26 for engaging a wrench, while its tubular extremity on the measuring gas end has external threading 27 for screwing the sensor into a tapped orifice of a measurement gas pipe not shown in the drawing.

A seal ring 29 is disposed on a shoulder 28 on the measurement gas side region of the interior space 12 of the metal casing 11. On the seal ring 29 there lies, properly sealed, the head 30 of a tubular solid electrolyte piece 31 of the sensor element 13, the measurement gas end of which (not shown) is closed off by the tip of the solid electrolyte piece. In the illustrated case the sensor element 13 is designed for measurement the oxygen partial pressure in the measurement gas as described in U.S. Pat. No. 4,347,113 already mentioned above.

The conductor path 32 disposed on the exterior of the solid electrolyte piece 31 terminates at its end remote from the measurement gas at the region of the seal ring 29 and the conductor path 33 disposed on the interior of the solid electrolyte piece 31 terminates at the end surface 34 of the solid electrolyte piece 31 remote from the measurement gas.

The contact flange 35 of the connection part 17 that is firm against twisting lies on top of the end surface 34 of the sensor element 13 remote from the measurement gas end of the element. The shaft 17/1 of the connection part 17 which runs axially in the metal casing 11 is bent in U-shape out of sheet metal and is prolonged at its end away from the measurement gas as an annular end section 17/2 in the region of the seal 24. On the region of this annular end section 17/2 away from the measurement gas is located the connection region 18 for the connecting cable 19. This cable 19, which is usually of Litz wire or other stranded wire is preferably fixed in this connection region 18 by crimping, while the end surface 36 of the insulation covering 37 surrounding the cable 19 towards the measurement gas end of the cable stands on the end surface 38 of the connection part 17 which is the more remote from the measurement gas. At the extremity remote from the measurement gas of the connection cable 19 surrounded with insulating covering 37, a connection element not shown in the drawing, is affixed, for example, a connection plug.

The electrically insulating tube 20 which surrounds a substantial part of the connection part 17 in its longitudinal bore 23 consists of an electrically insulating ceramic (e.g. sintered aluminum oxide) and stands with its end surface 39 at its measurement gas end on the side away from the measurement gas on the contact flange 35 of the connection part 17. The end section on the measurement gas end of the electrically insulated tube 20 is laterally confined in the interior 12 of the metal casing 11, while the section of the electrically insulating tube 20 away from the measurement gas end projects out of the section of the metal casing 11 away from the measurement gas, constituted as the stub tube 11/1. The end region 40 away from the measurement gas of the electrically insulating tube 20, which as the result of its external shoulder 22 has a diameter that is reduced compared to the main region of the electrically insulating tube 20 carries a seal element 41 remote from the measurement gas. The seal element 41 is made of yielding materials (e.g. PTFE) and is preferably a molded part which protrudes with its end section on the measurement gas end in to the longitudinal bore 23 of the electrically insulating tube 20 and supports itself by a head 42 on the end region 40 of the electrically insulating tube 20. The lateral surfaces of the head 42 are preferably of the shape of a cone frustum.

The seal element 41 surrounds the annular end section 17/2 of the connection part 17 in the lengthwise bore 43 of the seal 41 and extends all the way to the connectin region 18 of the connection part 17. The longitudinal bore 43 of the seal element 41 is of such dimensions that it surrounds essentially without play the annular end section 17/2 of the connection part 17, but nevertheless, does so in such a way that the seal element 41 can be pushed or slid without substantially expenditure of force onto the end section 17/2.

The enclosing shell 14 is pushed onto the tubular stub 11/1 of the metal casing 11, the enclosing shell consisting of a suitable sheet metal. It is fixed in place by means of bent-in tabs 44 holding in cavities 45 of the tubular stub 11/1. The hole 16 in the end 15 of the shell 14 remote from the measurement gas is broadened towards the shell interior in frustoconical shape and lies against the side of the seal element head 42 which is remote from the measurement gas. The enclosing shell 14 also has a shoulder 46 which supports itself on the dished annular spring 21 that rests on the external shoulder 22 of the electrically insulating tube 20. The tabs 44 of the enclosing shell 14 and the cavities 45 on the exterior of the metal casing tube stub 11/1 are so dimensioned that the dish spring 21 is mechanically biased, as the result of which the electrically insulated tube 20 presses hard against the contact flange 35 of the connecting part 17. In addition the head 30 of the sensor element is pressed fast and tight against the seal ring 29 lying against the metal casing shoulder 28.

The interior 47 of the enclosure casing 14 is of such dimension in its end regin 47/1 near its tip 15 that the end region 40 of the insulating tube 20 away from the measurement gas can be guided laterally thereinto. As the result of the mechanical bias exerted by the spring element 21 and the elasticity of the transverse bottom 15 and the adjoining region of the enclosure shell 14, the frustoconical hole 16 of the enclosing shell 14 is pressed fast and tight against the side of the seal element head 42 which faces away from the measurement gas.

This seal element 41 belonging to the seal 24 of the enclosing shell 14 remote from the measurement gas protrudes out of the hole 16 of the shell 14 in the form of a hollow shaft 48 and is provided externally with several coaxial ring grooves 49 molded into the part, which preferably have a sawtooth profile as shown in the drawing. The end surface of this seal element 41 away from the measurement gas is identified by the reference numeral 50.

A sealing tube 51 is pulled over the measurement gas end section of the connection cable 19 with its insulating ocvering 37 and over the sleeve-like connection region 18 of the connecting part 17 firmly surrounding the end section of the connection cable 19. The sealng tube 51 is made of a yielding material, as for example, PTFE. It can be pushed over the connection cable 19 and its insulating covering 37 and over the connection region 18 of the connecting part 17 without substantial exertion of force, so that it stands with its end surface towards the measurement gas against the end surface 50 of the seal element 41 facing away from the measurement gas.

An overlay sleeve 52, likewise made of a yielding material such as PTFE is also fitted with its middle bore 53 slipped over the insulating covering 37 of the connection cable 19 and laterally surrounds, in its middle bore 53, the sealing tube 51 without substantial play and, finally, with its region towards the measurement gas side, it surrounds the hollow shaft 48 of the sealing element 41. The internal surface of the measurement gas end region of the middle bore 53 is provided with a few coaxial ring ridges 54 which preferably have a sawtooth profile such that they are able to catch unreleasably in the sawtooth ring grooves 49 of the sealing element hollow shaft 48. The ring grooves 49 in the seal element 41 and the ring ridges 54 in the overlay shell 52 are dimensioned together with a stop surface 55 disposed away from the measurement gas in the middle bore 53 of the overlay shell, that the seal tube 51 is longitudinally distorted. As the result of this distortion of the tube 51 the end surface of that tube on the measurement gas side is pressed to make a tight seal on the measurement-gas-remote end surface 50 of the seal element 41 and the measurement-gas-remote end section of the seal tube 51 is pressed fast and tight against the middle bore 53 of the overlay shell 52 and against the insulating covering 37 of the connection cable 19. In the preferred embodiment the overlay shell middle bore 53 tapers down towards the measurement-gas-remote end of the overlay shell 52 and has a diameter in the region of the measurement gas remote end surface of the overlay shell 52 which corresponds to the external diameter of the connection cable insulating covering 37. The measurement-gas-near end section of the overlay shell 52 has a funnel-shaped widening 57 which tightly covers the frustoconical orifice 16 of the enclosing shell 14.

It should be mentioned that instead of the assembly-facilitating ring grooves 49 and ring ridges 44, other known methods of fastening (for example, a ring weld) can be used to fix the overlay shell 52 on the sealing element 41, so that it is not unconditionally essential for the overlay shell 52 to be made of a synthetic plastic and it can also bemade of a suitable metal. In the latter case, the funnel-shaped broadening 57 at the end of the overaly shell 52 can be fixed (e.g. also by welding) onto the frustoconical orifice 16 of the enclosing shell 14.

In addition, the remark should be made that the stressed seal 24 is suitable, not only for a sensor element 13 that has a solid electrolyte 31, but also for other sensor elements that can take advantage of a similar construction or of a corresponding disposition of parts.

Thus, it will be seen that although the invention has been described with reference to a particular illustrative embodiment, modifications and variations are possible within the inventive concept.

We claim:

1. A gas sensor suitable for mounting in the wall of a duct through which a gas to be measured as to its composition passes, comprising a metallic casing (11) of an external configuration having a central axis and being suitable for mounting in a duct wall, a sensor element (13) being held in said casing and projecting out therefrom to the measurement gas end of the sensor, a closure shell (14), being connected to said casing and extending therefrom away from said measurement gas end and having at its end closure away from said measurement gas end of the sensor a central aperture (16) which is aligned with said axis and through which a connection conductor leads out of the interior of the closure shell, said conductor being sealed in said aperture by a seal element (41) having an axial bore through which said conductor passes, and further comprising:

a metallic connection part (17) of elongated configuration, being aligned with said axis and at least partially surrounding said axis, being constituted so as to be rigid against torsion and being electrically connected to said sensor element (13) by contact with a conductor path (33) disposed on an interior surface of a solid electrolyte piece (31) thereof and extending, as a single centrally located outward leading metallic connection conductor for said sensor element, out of said casing (11) and through and out of said closure shell (14), passing through said bore of said element (41) and having a sleeve connection region (18) on a portion of said connection part protruding out of the measurement-gas-remote end of said seal element (41), a second conductor path of said sensor element being disposed on the exterior surface of said solid electrolyte piece (31);

a connection cable being electrically connected and fastened axially in said sleeve connection region (18) of said connection part (17), said cable having, beyond its fastening in said region of said connection part, an insulating covering (37);

a sealing tube (51), of yielding material of substantially constant wall thickness and capable of being slipped lengthwise into place, being disposed around said connection region (18) over said connection part (17) and over the adjacent insulation-covering end section of said connecting cable (19); and an overlay shell (52) having a close-fitting mid-bore (53) being forced over said sealing tube (51) so as to compress it inwardly while forcing it axially, to seal said midbore (53) and to seal the contact surface between said end of said seal element (41) and the adjacent end of said sealing tube.

2. Gas sensor according to claim 1, in which said overlay shell (52) has an internal stop surface (55) in said midbore which limits the end of said sealng tube (51) remote from said measurement gas, said sealing tube (51) standing with its other end against said end of said seal element (41), said overlay shell (52) surrounding said sealing tube (51) holding it practically without play in said midbore (53) and being fastened to said seal element (41).

3. Gas sensor according to claim 2, in which said internal stop surface (55) in said midbore (53) of said overlay shell (52) tapers down frustoconically towards the end of said overlay shell (52) remote from said measurement gas.

4. Gas sensor according to claim 2, in which the diameter of said midbore (53) of said overlay shell (52) in its end section away from the measurement gas is substantially the same as the outer diameter of said insulation covering (37) of said connection cable (19).

5. Gas sensor according to claim 1, in which said overlay shell (52) has an internal stop surface (55) in said midbore which limits the end of said sealing tube (51) remote from said measurement gas, said sealing tube (51) standing with its other end against said end of said seal element (41) said overlay shell (52) surrounding said sealing tube (51) holding it practically without play in said midbore (53) and being fastened to said closure shell (14).

6. Gas sensor according to claim 5, in which said internal stop surface (55) in said midbore (53) of said overlay shell (52) tapers down frustoconically towards the end of said overlay shell (52) remote from said measurement gas.

7. Gas sensor according to claim 5, in which the diameter of said midbore (53) of said overlay shell (52) in its end section away from the measurement gas is substantially the same as the outer diameter of said insulation covering (37) of said connection cable (19).

8. Gas sensor according to claim 1, in which said seal element (41) protrudes out of said aperture of said closure shell (14).

9. Gas sensor according to claim 8 in which the portion of said seal element (41) protruding out of said closure (14) is in the form of a hollow shaft (48) which is provided externally with at least one coaxial ring grove (49) formed therein, and in which at least one coaxial ring ridge (54) for catching in said ring groove (49) of said hollow shaft (48) is formed in an end section of said midbore (53) of said overlay shell (52).

10. A gas sensor according to claim 9 in which a plurality of ring grooves (49) are provided externally on said hollow shaft (48) of said seal element (41) and a corresponding plurality of ring ridges (54) are provided internally in said midbore (53) of said overlay shell (52), said ring grooves and ring ridges having interfitting sawtooth profiles so that by latching of said ridges in said grooves said overlay shell (52) is unreleasably connected to said seal element.

11. Gas sensor according to claim 10 in which said overlay shell (52) is made of a resilient material.

12. Gas sensor according to claim 9 in which said overlay shell (52) is made of a resilient material.

13. Gas sensor according to claim 1 in which the end section of said overlay shell extending towards said measurement gas covers said aperture (16) in said end closure (15) of said closure shell (14) by lying against the exterior of said end closure and supplementarily sealing said aperture and thereby backing up the seal provided by said seal element (41).

* * * * *